US00PP26342P3

(12) United States Plant Patent
DeGroot

(10) Patent No.: US PP26,342 P3
(45) Date of Patent: Jan. 19, 2016

(54) ***HYPERICUM* PLANT NAMED 'RUIHYG219A'**

(50) Latin Name: *Hypericum×Inodorum*
Varietal Denomination: RUIHYG219A

(71) Applicant: DeRUITER INTELLECTUAL PROPERTY B.V., Amstelveen (NL)

(72) Inventor: Hendrikus C. A. DeGroot, Amstelveen (NL)

(73) Assignee: De Ruiter Intellectual Property B.V., Amstelveen (NL)

( * ) Notice: Subject to any disclaimer, the term of this patent is extended or adjusted under 35 U.S.C. 154(b) by 122 days.

(21) Appl. No.: 13/998,421

(22) Filed: Oct. 30, 2013

(65) Prior Publication Data

US 2015/0121596 P1 Apr. 30, 2015

(51) Int. Cl.
*A01H 5/00* (2006.01)

(52) U.S. Cl.
USPC ..... Plt./442

(58) Field of Classification Search
USPC ..... Plt./442
See application file for complete search history.

*Primary Examiner* — Keith Robinson
(74) *Attorney, Agent, or Firm* — Barbara Campbell; Cochran Freund & Young LLC

(57) ABSTRACT

A new *Hypericum* plant particularly distinguished by red-pink berries and a compact pot plant, is disclosed.

2 Drawing Sheets

Genus and species: *Hypericum×Inodorum.*
Variety denomination: 'RUIHYG219A'.

BACKGROUND OF THE NEW PLANT

The present invention comprises a new and distinct variety of *Hypericum*, botanically known as *Hypericum×Inodorum*, and hereinafter referred to by the variety name 'RUIHYG219A'. 'RUIHYG219A' originated from an open-pollination conducted in June 2006 in Hazerswoude, The Netherlands between the proprietary female *Hypericum* variety 'Hp-01-0115-012' (unpatented), and an unknown, un-named male *Hypericum* variety.

The seeds from the open-pollination were sown and plants were grown outdoors for evaluation. An individual plant designated 'RUIHYG219A' was selected in October 2010. 'RUIHYG219A' was first vegetatively propagated in May 2009 in Hazerswoude, The Netherlands by softwood cuttings. 'RUIHYG219A' was found to reproduce true to type in successive generations of asexual propagation via softwood cuttings.

'RUIHYG219A' has not been made publicly available or sold more than one year prior to the filing date of this application.

SUMMARY

The following are the most outstanding and distinguishing characteristics of this new variety when grown under normal horticultural practices in Hazerswoude, The Netherlands.

1. Beautiful red-pink berries; and
2. A compact pot plant.

DESCRIPTION OF THE PHOTOGRAPHS

This new *Hypericum* plant is illustrated by the accompanying photographs which show the plant's overall plant habit including form, foliage, and berries. The photograph is of a one-year-old plant grown in outdoors in Hazerswoude, The Nertherlands in September 2010. The colors shown are as true as can be reasonably obtained by conventional photographic procedures.

Figure 1:
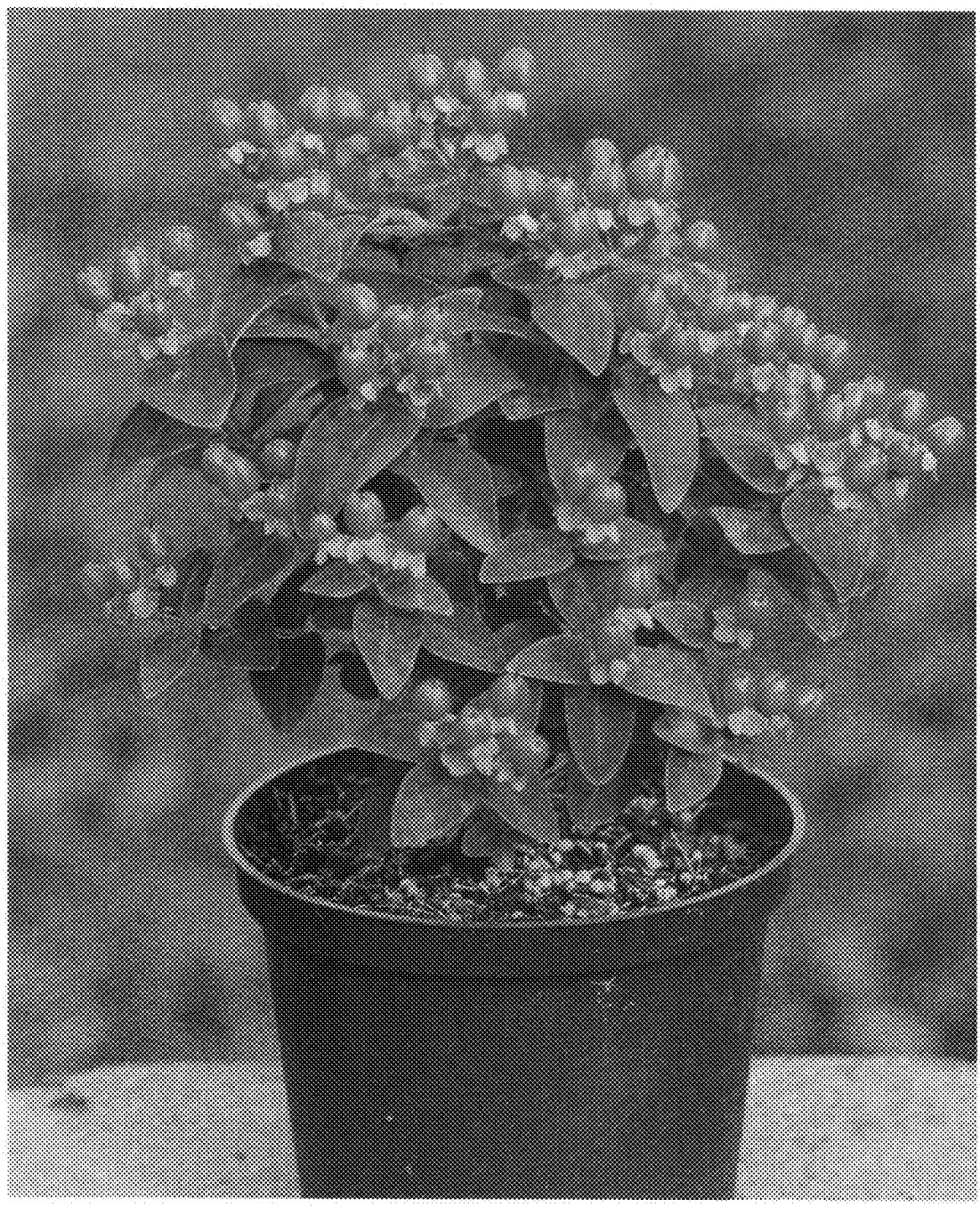
Figure 2:
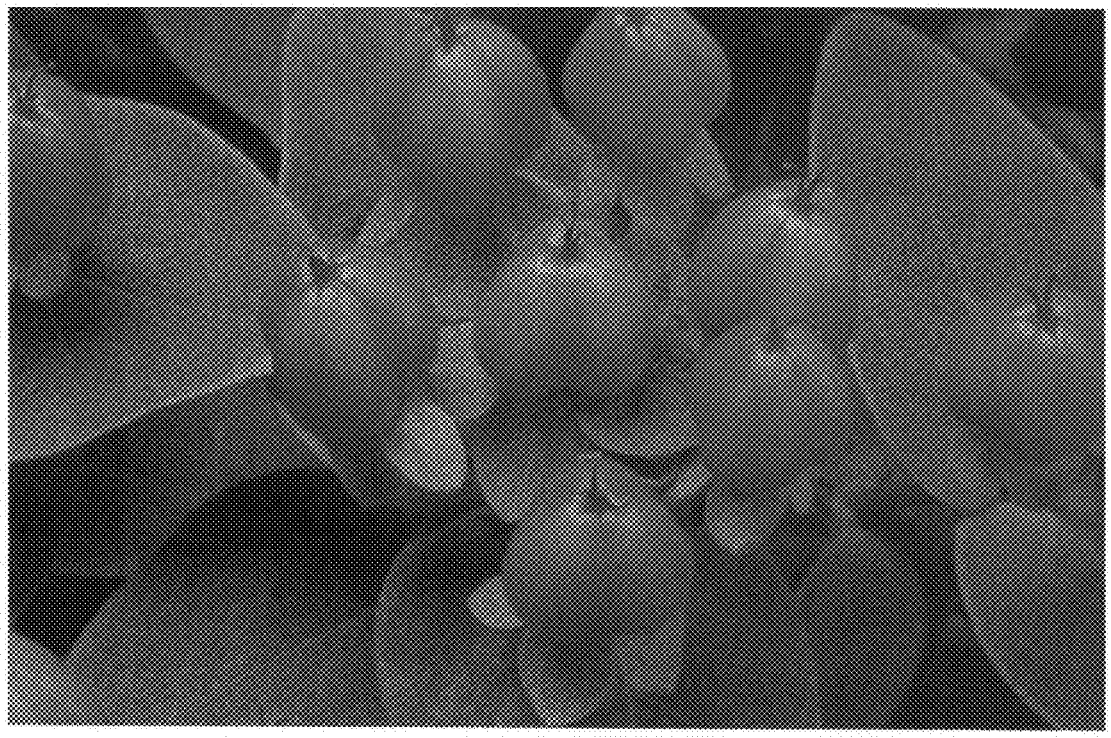

FIG. 1 shows the overall plant habit in a pot.
FIG. 2 shows a close-up of the foliage and berries.

DESCRIPTION OF THE NEW VARIETY

The following detailed descriptions set forth the distinctive characteristics of 'RUIHYG219A'. The data which define these characteristics were collected from one-year-old plants grown outdoors in Amstelveen, The Netherlands in September 2013. Color references are to The R.H.S. Colour Chart of The Royal Horticultural Society of London (R.H.S.), 1995.

Classification:
- *Family.*—Hypericeae.
- *Botanical.*—*Hypericum×Inodorum.*
- *Designation.*—'RUIHYG219A'.
- *Parentage.*—Female parent: The proprietary female *Hypericum* variety 'Hp-04-0115-012' (unpatented). Male parent: An unknown, un-named *Hypericum* variety.

Plant:
- *Form.*—Upright.
- *Habit.*—Dense, bushy.
- *Height (measured from the top of the soil).*—25.0 cm.
- *Width (horizontal plant diameter).*—25.0 cm.
- *Time to produce a finished plant.*—8 months.
- *Outdoor plant performance.*—For use in pots.
- *Time to initiate and develop roots.*—14 to 21 days.
- *Root description.*—Fibrous, well-branched; when young, are white, but older roots are RHS 165A (Brown).
- *Propagation type.*—Softwood cutting.
- *Growing season.*—Flowers in the summer and berries develop in September.

Stems:
- *Quantity per plant.*—Average is 12.
- *Strength.*—Strong.

*Length.*—About 18.0 cm.
*Internode length.*—3.0 cm.
*Diameter (from midpoint).*—About 3.0 mm.
*Color.*—RHS 174A.
*Texture.*—Smooth.
*Anthocyanin.*—Present, RHS 174A.

Leaves:
*Arrangement.*—Decussate.
*Length.*—5.0 cm.
*Width.*—4.0 cm.
*Shape.*—Cordate.
*Apex.*—Obtuse.
*Base.*—Cordate.
*Margin.*—Entire.
*Color, immature.*—Upper surface: RHS 137A. Lower surface: RHS 138B.
*Color, mature.*—Upper surface: RHS 139A. Lower surface: RHS 138B.
*Texture (both upper and lower surfaces).*—Smooth, rugose.
*Venation type.*—Pinnate.
*Venation color.*—Upper surface: RHS 145A. Lower surface: RHS 138C.
*Petiole.*—Absent.

Inflorescence:
*Type.*—Cyme, compound.
*Height.*—5.0 cm.
*Width.*—6.0 cm.
*Flowering season.*—Summer.
*Fragrance.*—Absent.
*Peduncle.*—Length: 7.0 mm. Diameter: 1.0 mm. Color: RHS 48A. Strength: Weak. Texture: Smooth.

Bud:
*Color.*—RHS 21B.
*Shape.*—Round.
*Height.*—0.7 cm.
*Diameter.*—0.7 cm.
*Texture.*—Smooth.

Flower:
*Depth.*—1.0 cm.
*Diameter.*—2.3 cm.
*Quantity per inflorescence.*—15.
*Petals.*—Arrangement and quantity of petals per flower: Single, composed of 5 petals per flower. Length: 1.3 cm. Width: 1.0 cm. Shape: Obovate. Apex: Rounded. Base: Cordate. Margin: Entire. Texture (both upper and lower surfaces): Smooth. Color (both immature and mature): Upper surface: RHS 13A. Lower surface: RHS 14C.

Calyx:
*Arrangement and quantity of sepals per flower.*—5.
*Shape.*—Flat.
*Sepals.*—Length: 0.8 cm. Width: 0.7 cm. Shape: Orbicular. Apex: Rounded. Base: Cordate. Margin: Entire. Texture (both upper and lower surfaces): Smooth. Color: Upper surface: RHS 146B. Lower surface: RHS 148B.

Pedicel:
*Length.*—1.0 cm.
*Diameter.*—0.15 cm.
*Color.*—RHS 180A.
*Texture.*—Smooth.

Reproductive organs:
*Stamens.*—Quantity per flower: About 60. Filament: Length: 0.6 cm. Width: 0.2 mm. Color: RHS 12A. Anther: Length: 0.1 cm. Width: 0.5 mm. Color: RHS 15A. Pollen amount: Moderate. Pollen color: RHS 13B.
*Pistil.*—Quantity per flower: 3. Length: 0.4 cm. Width: 5.0 mm. Stigma: Shape: globular. Color: RHS 179A. Quantity of stigma per pistil: 3. Style: Length: 0.3 cm. Color: RHS 153C. Ovary: Color: RHS 27B. Length: 6.0 mm. Width: 5.0 mm.

Fruit and seed set: Berries observed; 4 berries per inflorescence, berries are ovate in shape, triangular shaped in cross-section, berry surface texture is smooth, berries are glossy, 1.1 cm in length, 0.9 cm in width, and RHS 45A.

Disease and pest/insect resistance: No disease and pest/insect resistance observed or tested.

COMPARISON WITH PARENTAL LINE AND KNOWN VARIETY

'RUIHYG219A' is a distinct variety of *Hypericum* and is distinguished from its female parent as described in Table 1.

TABLE 1

Comparison with Parental Line

| Characteristic | 'RUIHYG219A' | Female Parent 'Hp-04-0115-012' |
|---|---|---|
| Berry shape | Ovate in shape but triangular in cross-section | Ovate |
| Berry color | Red-pink | Pink-red |

When 'RUIHYG219A' is compared to the commercial variety 'Seibig' (U.S. Plant Pat. No. 20,668), the following differences are described in Table 2.

TABLE 2

Comparison with Similar Variety

| Characteristic | 'RUIHYG219A' | 'Seibig' |
|---|---|---|
| Plant height | 25.0 cm | 70.0 cm |
| Plant width | 25.0 cm | 50.0 cm to 60.0 cm |

I claim:

1. A new and distinct variety of *Hypericum* plant designated 'RUIHYG219A' as illustrated and described herein.

* * * * *